US 6,626,671 B2

United States Patent
Klardie et al.

(10) Patent No.: US 6,626,671 B2
(45) Date of Patent: Sep. 30, 2003

(54) METHOD OF MANUFACTURING CUTTING FLUTES ON A COATED OR ROUGHENED DENTAL IMPLANT

(75) Inventors: Michael R. Klardie, Bloomington, MN (US); Jeremy M. Huotari, Cologn, MN (US); Thomas A. Tremmel, Minneapolis, MN (US); Peter B. Swanson, Eden Prairie, MN (US)

(73) Assignee: Lifecore Biomedical, Inc., Chaska, MN (US)

(*) Notice: Subject to any disclaimer, the term of this patent is extended or adjusted under 35 U.S.C. 154(b) by 124 days.

(21) Appl. No.: 09/976,263

(22) Filed: Oct. 11, 2001

(65) Prior Publication Data

US 2002/0061494 A1 May 23, 2002

Related U.S. Application Data

(60) Provisional application No. 60/239,346, filed on Oct. 11, 2000.

(51) Int. Cl.⁷ .................................................. A61C 8/00
(52) U.S. Cl. ................. 433/201.1; 433/173; 433/174
(58) Field of Search ....................... 433/172, 173, 433/174, 175, 176, 201.1

(56) References Cited

U.S. PATENT DOCUMENTS

| 5,201,656 | A | * | 4/1993 | Sicurelli, Jr. | 433/173 |
|---|---|---|---|---|---|
| 5,571,017 | A | | 11/1996 | Niznick | 433/174 |
| 5,829,978 | A | * | 11/1998 | Day | 433/173 |
| 5,876,453 | A | | 3/1999 | Beaty | 623/16 |
| 5,885,079 | A | | 3/1999 | Niznick | 433/172 |
| 5,947,735 | A | * | 9/1999 | Day | 433/173 |
| 5,989,027 | A | | 11/1999 | Wagner et al. | 433/173 |
| 6,048,204 | A | | 4/2000 | Klardie et al. | 433/174 |
| 6,095,817 | A | | 8/2000 | Wagner et al. | 433/173 |
| 6,102,703 | A | | 8/2000 | Day | 433/174 |
| 6,220,861 | B1 | * | 4/2001 | Kwon et al. | 433/173 |

OTHER PUBLICATIONS

U.S. patent application Ser. No. 60/239,346, Klardie et al., filed Oct. 11, 2000.

* cited by examiner

Primary Examiner—Cary E. O'Connor
(74) Attorney, Agent, or Firm—Dorsey & Whitney LLP

(57) ABSTRACT

A dental implant may be prepared by roughening or coating a desired portion of a dental implant blank and removing material from the dental implant blank subsequent to roughening the dental implant blank. By removing material, a cutting flute with a cutting edge, cutting surface and collector surface may be formed. The cutting surface and collector surface is relatively smooth compared to the cutting edge.

38 Claims, 3 Drawing Sheets

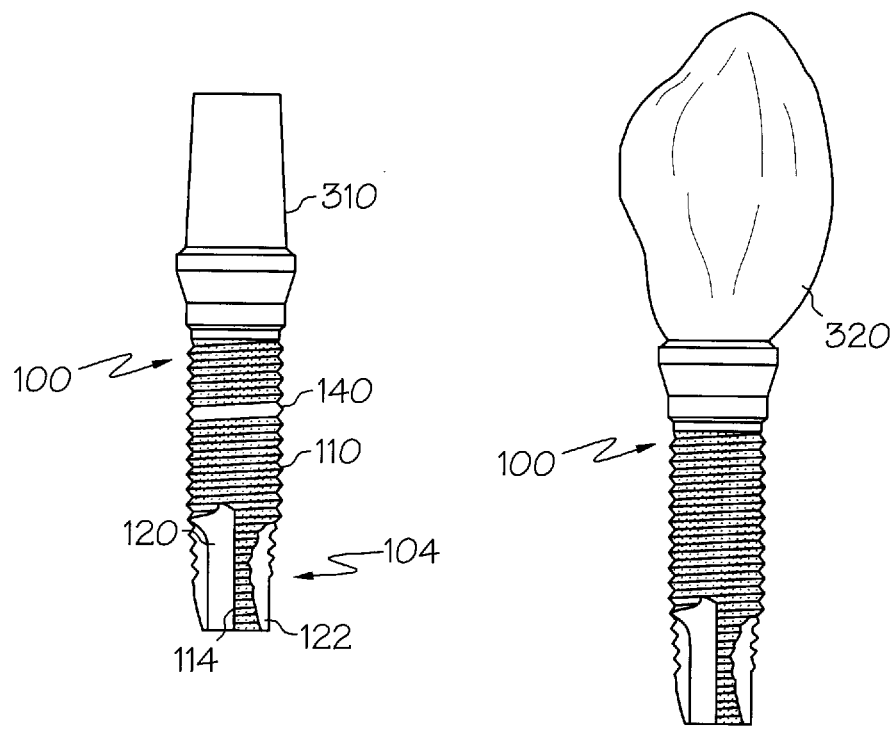
FIG. 5
FIG. 9
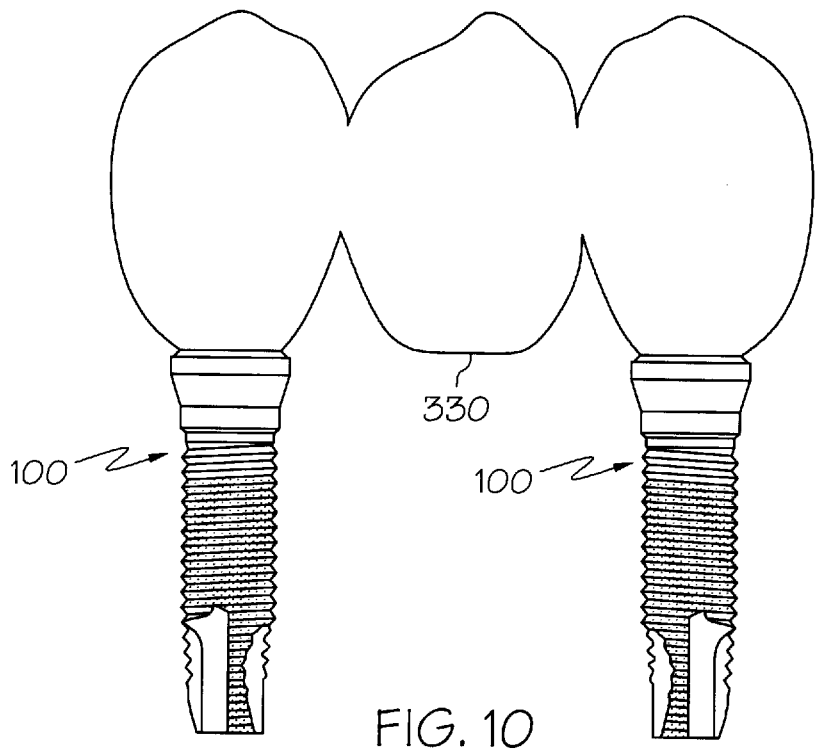
FIG. 10

METHOD OF MANUFACTURING CUTTING FLUTES ON A COATED OR ROUGHENED DENTAL IMPLANT

CROSS-REFERENCE TO RELATED APPLICATIONS

This application claims priority from U.S. provisional application No. 60/239,346, filed Oct. 11, 2000, the entire contents of which are incorporated herein by reference.

BACKGROUND OF THE INVENTION

The use of dental implants having a roughened surface has been disclosed in a number of patents including U.S. Pat. No. 6,102,703, U.S. Pat. No. 6,095,817, U.S. Pat. No. 6,048,204, U.S. Pat. No. 5,989,027, U.S. Pat. No. 5,947,735, U.S. Pat. No. 5,876,453 and U.S. Pat. No. 5,571,017. It is believed that the roughened surface facilitates osseointegration of the implant and surrounding bone and also aids in mechanical retention of the implant at the time of placement. The term 'roughening' and its cognates is intended to refer to surface texture on the order of about a hundred of microns or less. Surface roughening is not intended to refer to larger features of an implant such as the thread.

A number of different methods of roughening and/or coating the surface of an implant are known. One such method involves the use of a titanium plasma spray (TPS). The titanium plasma spray coating significantly increases the surface area of the implant. TPS both roughens and coats the implant.

Another method of roughening an implant involves blasting the implant with a resorbable blast material such as a calcium phosphate medium. The surface of the implant may then be passivated.

Other treatments using forms of hydroxyapatite for coating and/or roughening an implant without any subsequent passivation are also known.

Yet another method of roughening an implant involves acid etching the implant. One or more acids, for example, a combination of hydrochloric acid and sulfuric acid, may be used to etch an implant and thereby roughen the implant.

Other methods of surface roughening include blasting the implant with a blast material such as sand, glass, aluminum blast material including aluminum oxide ($Al_2O_3$) or titanium oxide ($TiO_2$). Alternative blast media including calcium carbonate, sodium bicarbonate or other blast media that can be dissolved readily in a solution, typically an acidic solution. The solution should be able to substantially remove 100% of any particulate matter from the roughened surface.

Ion etching, chemical milling, laser etching and spark erosion techniques have also been used to roughen surfaces of implants.

Any of the above methods may include a passivation step and/or a cleaning step following roughening of the implant.

One type of implant to which roughening is applied is the self-tapping dental implant. Typically, self-tapping implants are formed by machining a one or more cavities in an implant body near the distal end of the implant. The cavities provide cutting edges which cut surrounding bone as the implant is threaded into the bone. The cavities also hold bone material that has been cut by the implant.

Roughening of the outer surface of the implant, however, can lead to rounding of the cutting edges of the implant, decreasing the cutting efficiency of the edges and increasing the torque required to insert the implant. A number of different techniques have been disclosed to avoid this problem. U.S. Pat. No. 5,885,079 and U.S. Pat. No. 5,571,017 disclose roughened implants having distal ends which are not as rough as the middle portion of the implants. U.S. Pat. No. 5,1947,735 discloses an implant having cutting edges which are substantially free of roughening. The cutting edges are masked during the roughening process.

There remains a need for methods of making self-tapping implants which are roughened and yet have sharp cutting edges.

All U.S. patents and applications and all other published documents mentioned anywhere in this application are incorporated herein by reference in their entirety.

The invention in various of its embodiment is summarized below. Additional details of the invention and/or additional embodiments of the invention may be found in the Detailed Description of the Invention below.

The abstract provided herewith is intended to comply with 37 CFR 1.72 and is not intended be used in determining the scope of the claimed invention.

BRIEF SUMMARY OF THE INVENTION

In at least one embodiment, the invention is directed to a method of preparing a dental implant made from a material. In accordance with the method, a dental implant blank having a proximal and a distal end and a surface is provided. A desired portion of the surface of the dental implant blank is roughened and/or coated. Subsequent to roughening or coating, material is removed from at least a portion of the dental implant blank to form a dental implant. One or more cutting flutes may be formed during the removing step. In some embodiments of the invention however, the implant blank is machined without the cutting flute configuration. Each cutting flute comprises a cutting surface, a collector surface and a cutting edge. The cutting surface and collector surface are relatively smooth compared with the cutting edge. Desirably, the one or more cutting flutes are at the distal end of the implant.

The roughening or coating step may be accomplished by any suitable treatment process including titanium plasma spray processing, acid etching, blasting with a resorbable blast material, such as a medium having calcium phosphate, blasting with a non-resorbable blast medium or any combination of the above treatment processes. Following roughening, the dental implant blank may be passivated and/or cleaned to remove any particulate matter or any other undesirable matter. The dental implant may also be coated with a suitable coating such as hydroxyapatite.

In at least one embodiment, the cutting flutes are machined into the roughened dental implant blank after the roughening or coating step. In some embodiments, after formation of the cutting flutes, the implant may again be roughened to increase the surface roughness within the cutting region.

In some embodiments of the invention a sleeve may be threaded onto the apical or distal end of the implant. Preferably, the sleeve is threaded onto the distal end following the initial roughening treatment. The cutting flutes may then be machined into the implant through the sleeve. By machining the cutting flutes through the sleeve the potential formation of metal burrs is prevented.

In at least one embodiment of the invention, after the cutting flutes have been machined into the implant the sleeve may be removed and the implant may be roughened again to increase the surface roughness of the cutting flute region.

Alternatively, the sleeve may remain on the implant through the second roughening step to act as a masking feature. Following the second roughening step the sleeve may then be removed.

Desirably, the dental implant blank includes a neck portion at the proximal end and the roughened and/or coated portion of the dental implant blank extends from the distal end of the dental implant blank toward the proximal end of the dental implant blank, terminating distal to the neck portion. More desirably, the roughened portion and/or coated portion terminates one or two threads down from the neck portion or 1.5 mm to 3 mm down from the neck portion. The invention also contemplates the roughened and/or coated portion extending to the neck portion of the dental implant blank.

Optionally, the method further comprises the step of disposing a restorative object on the dental implant.

In another embodiment, the invention is directed to a method of preparing a dental implant. In accordance with the invention, a dental implant blank having a roughened and/or coated portion is provided and material removed from at least a portion of the roughened and/or coated blank to form a dental implant. Desirably, the neck portion of the implant blank is smooth. The dental implant blank may be roughened using a titanium plasma spray, a resorbable blast medium, such as calcium phosphate or any other suitable technique. The blank may be coated using hydroxy apatite or any other suitable coating. Desirably, material is removed to form at least one cutting flute in the distal end. Also desirably, the cutting flute comprises a cutting surface terminating in a rough cutting edge and a collector surface with the cutting surface and collector surface smoother than the cutting edge. The dental implant may be threaded or unthreaded.

An embodiment of the invention is also directed to an implant made using the inventive methods.

Some embodiments of the invention are directed to a dental implant comprising at least one roughened portion and/or coated portion, the implant having at least one cutting flute therein, the cutting flute including a roughened and/or coated cutting edge. Desirably, the cutting flute includes a cutting surface and a collector surface adjacent to the cutting face, wherein at least a portion of one of the cutting surface and the collector surface is smooth or smoother than the roughened and/or coated portion of the implant. The dental implant may optionally be self-tapping. The dental implant may further comprise a restorative disposed at the proximal end of the implant.

BRIEF DESCRIPTION OF THE SEVERAL VIEWS OF THE DRAWING(S)

A detailed description of the invention is hereafter described with specific reference being made to the drawings in which:

FIG. 5 is a side elevational assembly showing an inventive implant with an abutment mounted thereon and a relatively smooth band in the middle portion;

FIG. 9 is a side elevational assembly showing an inventive implant with a tooth mounted thereon;

FIG. 10 is a side elevational assembly showing an inventive implant with a bridge mounted thereon;

DETAILED DESCRIPTION OF THE INVENTION

Figure 1:
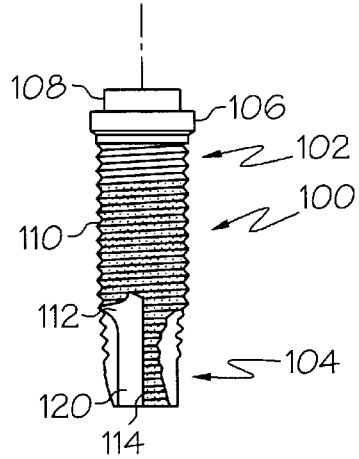
FIG. 1 is a side elevational view of the self tapping dental implant according to the present invention.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, unless otherwise indicated, identical reference numerals used in different figures refer to the same component. Also, in the embodiments of FIGS. 1–5, 9 and 10, the roughened surface is indicated by the presence of dots while in the embodiments of FIGS. 6–8 and 11–13 the roughened surface is indicated by a lighter shading.

Figure 2:
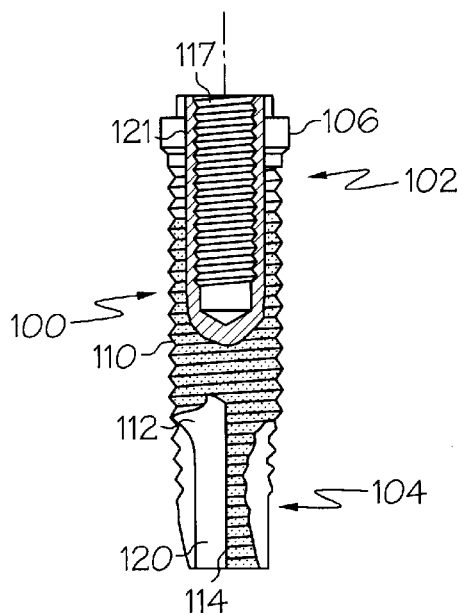
FIG. 2 is a side elevational view with parts cut away of an embodiment of the self tapping screw type dental implant according to the present invention.
Figure 3:
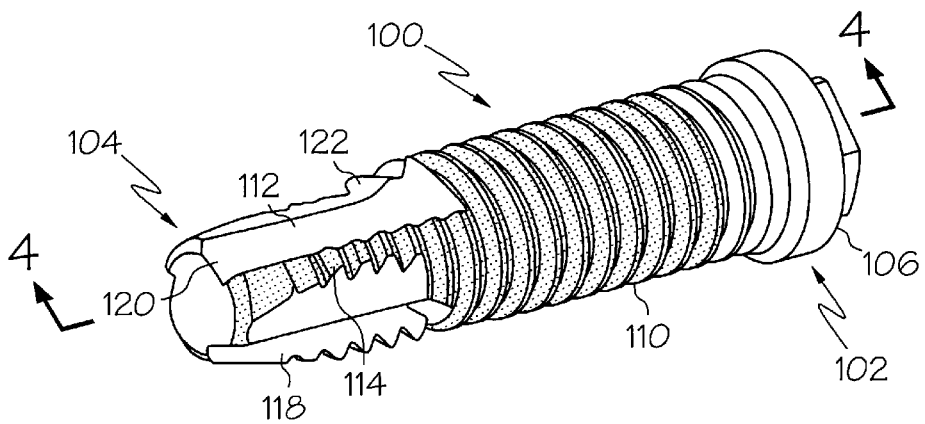
FIG. 3 is a perspective view of the inventive implant shown in FIG. 1.
Figure 4:
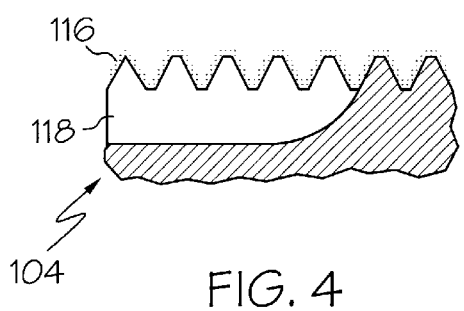
FIG. 4 is an alternate fragmentary profile of the implant of FIG. 4 taken along line 4—4.

The instant invention is directed in one embodiment to a dental implant such as that shown generally at 100 in FIGS. 1–4. The implant is intended to be inserted in a bored hole in the jaw for permanent anchoring of artificial teeth, toothbridges and other dental implants. Implant 100 includes proximal end 102 and distal end 104. Proximal end 102 includes neck 106 and wrench engaging surface 108. An attachment means for attaching a dental prosthesis thereto is provided at the proximal end. As depicted in FIG. 2, the attachment means is a bore 117 within proximal end 102, the bore being threaded 121 to accept threaded inserts. The attachment means may be of any other suitable design for attaching a dental prosthesis such as a male part extending upwards from the upper portion. Optionally, the male part may be threaded.

A threaded middle 110 portion extends from the distal end of the neck to the proximal end of cutting flutes 112. A portion 114 of distal end 104 of the implant is also threaded. Distal end 104 includes three cutting flutes. Cutting flutes 112 include a cutting edge 116, shown in FIG. 3, a cutting surface 118 and a collector surface 120. An optional beveled relief surface 122 is also provided.

At least a portion of middle portion 110 of implant 100 is roughened and/or coated as is distal portion 114 of the implant. Desirably, the roughening and/or coating extends to within 1.5 mm to 3 mm of the neck portion or to within one or two threads of neck 106, as shown in FIG. 1. The invention also contemplates the roughening and/or coating extending to the neck of the implant, as shown in FIGS. 5 and 9. At the distal portion, cutting edge 116 is roughened and/or coated. Cutting surface 118, collector surface 120 and beveled relief surface 122 are smooth. Desirably, neck 106 is smooth.

The surface of the cutting flute are smooth in the embodiment of FIG. 1. The invention also contemplates embodiments in which only a portion of the surfaces of the cutting flute are smooth. For example, the beveled relief surface may be roughened and/or coated while the cutting surface and collector surface are smooth.

More generally, the invention is directed to a dental implant having at least one cutting flute and desirably a plurality of cutting flutes with a roughened cutting edge, at least a portion of the cutting flute being relatively smooth compared to the roughened cutting edge. Desirably, at least a portion of one of the cutting surface and the collector surface of the cutting flute is smooth. More desirably, both the cutting surface and the collector surface of the cutting flute are smooth, as shown in FIG. 1.

The inventive implants may have optional bands or sections which are less rough than the remainder of the roughened surfaces. Desirably, such bands are relatively smooth compared to the roughened surfaces. As shown, for example, in FIG. 5, implant 100 includes at least unroughened circumferential band 140 along the implant. Implant 100 further comprises an abutment 310 disposed at the proximal end. Desirably, as shown in FIG. 5, bands 140 are in middle portion 110 of the implant. Distal end 104 of the implant including cutting edges 114 which are roughened. Cutting surface 118, collector surface 120 and optional relief surface 122 are relatively smooth compared with the roughened surfaces.

Desirably, the roughened portions have an average surface roughness of approximately 6–9 microns as measured from the peak to the valley of the surface roughening where the surface is roughened using resorbable blast material, such as for example calcium phosphate, and an average surface roughness of approximately 10–20 microns where a titanium plasma spray is used. Smooth portions desirably exhibit an average roughness of no more than approximately 3–4 microns.

The invention also contemplates roughening portions of the surface to roughnesses of between about 20 microns and 100 microns or more.

Bands 140 may be left unroughened by placing a mask about the implant in the desired region of the implant prior to roughening the implant.

The invention is also directed to implants having one or more circumferential bands which are smooth relative to roughened portions adjacent to the bands or bands which are uncoated.

The inventive dental implants may be made of Ti-6A1-4V E.L.I. (ASTM F136) or commercially pure titanium (ASTM F67) grade 3. Other grades of commercially pure titanium such as grades 1, 2 and 4 of commercially pure titanium (ASTM F67) may also be used depending on the desired shape and strength characteristics of the implant. Any other suitable biocompatible materials may be used as well.

The implant may be cylindrical, substantially cylindrical, tapered toward one or both ends or any other suitable shape.

The invention is directed toward threaded and non-threaded implants and methods of making the same. Where the implant is threaded, the thread may be a v-thread, square thread, buttress thread, ACME thread or any other thread pattern.

The inventive implants may further comprise a restorative disposed at the proximal end of the implant. Examples of restorative objects include abutment 310 shown in FIG. 5, artificial teeth 320 shown in FIG. 9 and bridges 330 shown in FIG. 10.

Figures 6, 7, 8:
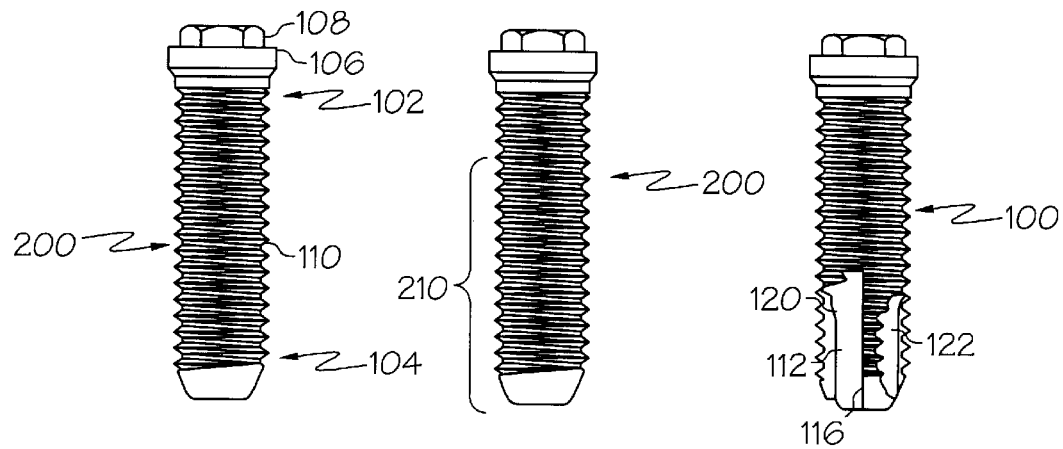
FIG. 6 is a side elevational view of a dental implant blank prior to processing with the inventive methods.
FIG. 7 is a side elevational view of a roughened dental implant blank.
FIG. 8 is a side elevational view of an inventive dental implant prepared from the dental implant blank of FIGS. 6 and 7 in accordance with the inventive methods disclosed herein.

The invention is also directed to inventive methods for making dental implants. In accordance with one such inventive method of preparing a dental implant, a roughened blank such as that shown at 200 in FIG. 6 is provided. As shown in FIG. 7, a portion 210 of blank 200 is roughened using any suitable process know in the art including using a titanium plasma spray (TPS), a resorbable blast material (RBM) or any of the other techniques discussed above. The blank may be coated at least in part via the application of hydroxyapatite thereto. One or more cutting flutes 112 are then cut into blank to produce dental implant 100 shown in FIG. 8. Cutting flutes 112 include a cutting surface 118 with a roughened cutting edge 116 and a collector surface 120. Optionally, a beveled relief surface 122 may also be provided. Cutting surface 118 and collector surface 120 are smooth relative to the roughened and/or coated portion of the implant. Alternatively, after formation of the cutting flutes 112, the implant may again be roughened to increase the surface roughness within the cutting surface 118.

Figures 11, 12, 13:
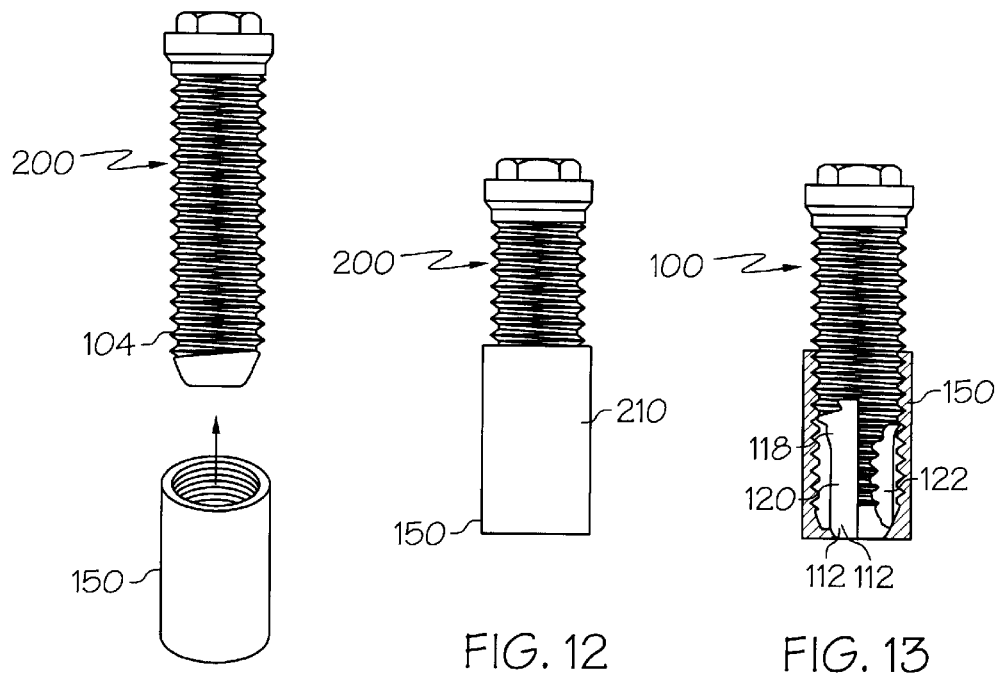
FIG. 11 is an exploded side elevational view of a dental implant blank and sleeve prior to placing the sleeve on the blank for processing with the inventive methods.
FIG. 12 is a side elevational view of a blank and sleeve assembly.
FIG. 13 is a side elevational view of the blank and sleeve assembly shown in FIG. 13, wherein portions of the blank and sleeve have been removed according to the inventive methods.

In some embodiments of the invention, a sleeve 150 may be slid or threaded onto the apical or distal end 104 of the blank 200 such as is shown in FIG. 11. Preferably, the sleeve 150 is threaded onto the roughened portion 210 following the initial roughening treatment as shown in FIG. 12. The cutting flutes 112 may then be machined into the blank through the sleeve 150 to form implant 100 such as is shown in FIG. 13. By machining the cutting flutes 112 through the sleeve 150 the potential formation of metal burrs is prevented.

In at least one embodiment of the invention after the cutting flutes 112 have been machined into the implant 100 the sleeve 150 may be removed and the implant may be further roughened to increase the surface roughness of the implant 100. Alternatively, sleeve 150 may remain on the implant 100 through the second roughening step to act as a masking feature to ensure that additional roughening is provided only to the cutting surface 118 and/or to the optional collector surface 120 and/or beveled relief surface 122. Following the second roughening step sleeve 150 may then be removed.

In the various embodiments discussed, following roughening and/or coating, the surface may be passivated and/or cleaned. The surface may be passivated by exposing the blank to a 30% nitric acid solution. Cleaning may be accomplished ultrasonically to remove particulate matter and any other undesirable matter from the blank. Other passivation and cleaning processes, as are known in the art, may also be used. Where the surface is roughened using TPS, no passivation is necessary.

In another embodiment, the invention is directed to a method of preparing a dental implant. The inventive method comprises the steps of providing a dental implant blank made of a material and having a roughened and/or coated portion. The blank has a proximal and a distal end. Material is removed from at least a portion of the distal end of the roughened and/or coated portion of the blank. Desirably, the material is removed from the distal end of the blank to form one or more cutting flutes with cutting surfaces terminating in cutting edges and collector surfaces. The cutting edges of the resulting implant are rough while the cutting surfaces and collector surfaces are relatively smooth compared to the rough and/or coated portions of the implant.

In accordance with one embodiment of the invention, a threaded implant blank may be machined without cutting flutes. The implant surface may be roughened using any suitable roughening process. Following the roughening and/or coating process, cutting flutes are milled into the implants.

This produces a roughened and sharp cutting edge, which can efficiently cut a threaded path into bone for self-tapping an implant. In some embodiments of the invention, the inner surfaces of the cutting flutes have a machined surface produced by the milling, but are not roughened. The inner surfaces of the cutting flutes do not engage the surrounding bone of the surgical site. Therefore, they do not contribute to surface drag or increased torque seating torque requirements.

In accordance with another embodiment of the inventive method, a dental implant blank is provided and one or more cutting flutes having a cutting surface, a collector surface, a cutting edge and optionally, a beveled relief surface are cut into the blank to form an in-process dental implant. The in-process dental implant is then subjected to any of the above roughening or coating processes. The roughening and/or coating may be limited to the distal end of the implant, including the cutting edge, the cutting surface, the collector surface and where present, the beveled relief surface, or may extend into to the middle portion of the implant and, optionally, up to the neck of the in-process dental implant, to within 1.5–3 mm of the neck or to within 1 to 2 threads of the neck. A dental implant is then made from the in-process dental implant by removing a thin layer of material from the roughened and/or coated cutting surface of the in-process dental implant to smooth the cutting surface. A thin layer of material may also optionally be removed from the roughened collector surface and/or optional beveled relief surface. The resulting implant has one or more rough cutting edges and relatively smooth cutting surfaces.

In accordance with yet another embodiment of the invention, a method is provided for preparing a dental implant in which a dental implant blank is provided and one or more beveled relief surfaces cut into the blank. At least a portion of the resulting in-process dental implant is then roughened and/coated using any of the roughening and/or coating process described above. The roughening and/or coating may be limited to the distal end of the implant or may extend into to the middle portion of the implant and, optionally, up to the neck of the in-process dental implant, to within 1.5–3 mm of the neck or to within 1 to 2 threads of the neck. A cutting flute is then cut adjacent each beveled relief surface. The cutting flutes each have a cutting surface, a collector surface and a cutting edge. The resulting dental implant has one or more rough cutting edges and relatively smooth cutting surfaces.

The invention is also directed to dental implants made in accordance with any of the above methods.

In addition to the specific embodiments claimed below, the invention is also directed to other embodiments having any other possible combination of the dependent features claimed below.

The above disclosure is intended to be illustrative and not exhaustive. The description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A method of preparing a dental implant made from a material comprising the steps of
    providing a dental implant blank having a proximal and a distal end and a surface;
    treating a desired portion of the surface of the dental implant blank by roughening and/or coating the portion of the dental implant blank;
    placing a sleeve about the desired portion of the surface of the dental implant blank
    removing material from at least a portion of the dental implant blank subsequent to the treating step to form a dental implant, the removing step removing material from at least a portion of the sleeve and the at least a portion of the dental implant blank thereunder.

2. The method of claim 1 further comprising the step of treating the at least a portion of the dental implant blank subsequent to the removing step by roughening and/or coating the at least a portion of the dental implant.

3. The method of claim 2 further comprising the step of removing the sleeve from about the desired portion of the surface of the dental implant blank subsequent to the step of treating the at least a portion of the dental implant blank.

4. The method of claim 2 further comprising the step of removing the sleeve from about the desired portion of the surface of the dental implant blank subsequent to the removing step and prior to the step of treating the at least a portion of the dental implant blank.

5. A method of preparing a dental implant made from a material comprising the steps of
    providing a dental implant blank having a proximal and a distal end and a surface;
    treating a desired portion of the surface of the dental implant blank by roughening and/or coating the portion of the dental implant blank;
    removing material from at least a portion of the dental implant blank subsequent to the treating step to form a dental implant, wherein one or more cutting flutes are formed during the removing step.

6. A dental implant made in accordance with the method of claim 1.

7. The method of claim 5 wherein each cutting flute comprises a cutting surface, a collector surface and a cutting edge, the cutting surface and collector surface relatively smooth compared with the cutting edge.

8. The method of claim 7 wherein the dental implant blank is roughened by a treatment process selected from the group consisting of titanium plasma spray processing, acid etching, blasting with a resorbable blast material, blasting with a non-resorbable blast medium or combinations thereof.

9. The method of claim 7 wherein the dental implant blank is roughened via titanium spray processing.

10. The method of claim 7 wherein the dental implant blank is roughened via the use of a resorbable blast material.

11. The method of claim 7 further comprising the step of passivating the dental implant blank following the roughening step.

12. The method of claim 7 further comprising the step of cleaning the dental implant blank following the roughening step.

13. The method of claim 7 wherein the dental implant blank includes a neck portion at the proximal end and the treated portion of the dental implant blank extends from the distal end of the dental implant blank toward the proximal end of the dental implant blank, terminating distal to the neck portion.

14. The method of claim 5 wherein the cutting flutes are at the distal end of the implant.

15. The method of claim 14 wherein the dental implant blank includes a neck portion at the proximal end and the treated portion of the dental implant blank extends from the distal end of the dental implant blank toward the proximal end of the dental implant blank, terminating at the neck portion.

16. The method of claim 14 wherein the dental implant blank includes a neck portion at the proximal end and the treated portion of the dental implant blank extends from the distal end of the dental implant blank to within 1.5 to 3 mm of the neck portion.

17. The method of claim 14 wherein the dental implant blank includes a body portion with threads disposed about the body portion and a neck portion at the proximal end and the treated portion of the dental implant blank extends from the distal end of the dental implant blank to within 1 to 2 threads of the neck portion.

18. The method of claim 14 further comprising the step of disposing a restorative object on the dental implant.

19. The method of claim 5 further comprising the step of treating at least a portion of the dental implant subsequent to the removing step by roughening and/or coating the at least a portion of the dental implant.

20. The method of claim 19 wherein the at least a portion of the dental implant is at least a portion of the one or more cutting flutes.

21. A method of preparing a dental implant comprising the steps of:
providing a dental implant blank having a treated portion selected from the group consisting of roughened portions and coated portions, the blank having a proximal and a distal end;
removing material from at least a portion of the dental implant blank to form a dental implant, wherein during the removing step, material is removed to form at least one cutting flute in the distal end.

22. The method of claim 21 wherein the dental implant blank has a smooth neck portion at the proximal end.

23. The method of claim 21 wherein the dental implant blank includes a body portion and threads disposed about the body portion.

24. The method of claim 21 wherein the material is removed from the distal end of the implant blank to form at least one cutting flute therein.

25. The method of claim 24 wherein the at least a collector surface, the cutting flute comprises a cutting surface terminating in a rough cutting edge and a collector surface, the cutting surface and collector surface smoother than the cutting edge.

26. A dental implant made in accordance with the method of claim 21.

27. A dental implant comprising at least one treated portion selected from the group consisting of roughened portions and coated portions, the implant having at least one cutting flute therein, the cutting flute including a roughened cutting edge, a cutting surface and a collector surface adjacent to the cutting face, wherein at least a portion of one of the cutting surface and the collector surface is smooth.

28. A dental implant comprising at least one treated portion selected from the group consisting of roughened portions and coated portions, the implant having at least one cutting flute therein, the cutting flute including a roughened cutting edge, the cutting flute including a cutting surface and a collector surface adjacent to the cutting face, wherein the cutting surface and the collector surface are smoother relative to the treated portion.

29. The dental implant of claim 28 wherein the implant is self-tapping.

30. The dental implant of claim 28 wherein the treated portion is a roughened portion.

31. The dental implant of claim 30 further comprising a restorative disposed at the proximal end of the implant, the restorative object selected from the group consisting of abutments, artificial teeth, and bridges.

32. A method of preparing a dental implant comprising the steps of: providing an in-process dental implant comprising at least one cutting flute, the cutting flute comprising a cutting surface, a collector surface and a cutting edge roughening and/or coating at least the cutting surface and cutting edge of the in-process dental implant; and removing at least a layer of material from the cutting surface so that the cutting surface is relatively smooth compared to the cutting edge.

33. The method of claim 32 wherein the cutting flute includes a beveled relief surface.

34. The method of claim 32 wherein the implant includes a neck and the in-process dental implant is roughened and/or coated to within 1.5 mm to 3 mm of the neck.

35. A dental implant made in accordance with the method of claim 34.

36. A method of preparing a dental implant comprising the steps of: providing a dental implant blank having a distal end with one or more beveled relief surfaces; roughening and/or coating at least the distal end of the implant; and cutting a cutting flute adjacent each of the one or more beveled relief surfaces.

37. The method of claim 36 wherein the implant includes a neck and the blank is roughened and/or coated to within 1.5 mm to 3 mm of the neck.

38. A dental implant made in accordance with the method of claim 36.

* * * * *

UNITED STATES PATENT AND TRADEMARK OFFICE
CERTIFICATE OF CORRECTION

PATENT NO.     : 6,626,671 B2                                   Page 1 of 1
DATED          : September 30, 2003
INVENTOR(S)    : Michael R. Klardie et al.

It is certified that error appears in the above-identified patent and that said Letters Patent is hereby corrected as shown below:

<u>Column 2,</u>
Lines 3-4, "U.S. Pat. No. 5,1947,735" should be -- U.S. Pat. No. 5,947,735 --

<u>Column 9,</u>
Lines 47-48, "at least a collector surface, the cutting" should be -- at least one cutting --

<u>Column 10,</u>
Lines 26 and 42, "of: providing" should be -- of providing --

Signed and Sealed this

Sixteenth Day of March, 2004

JON W. DUDAS
*Acting Director of the United States Patent and Trademark Office*